United States Patent [19]

Lloyd et al.

[11] 4,135,023
[45] Jan. 16, 1979

[54] EMBOSSED FILM PRODUCT AND ADHESIVE COATED STRIP FORMED THEREFROM

[75] Inventors: Ronald Lloyd, Sawbridgeworth; Albert G. Patchell, Welwyn Garden City; William O. Murphy, Sawbridgeworth; Peter J. Herbert, Bishops Stortford, all of England

[73] Assignee: Smith & Nephew Plastics Ltd., Harlow, England

[21] Appl. No.: 780,917

[22] Filed: Mar. 24, 1977

Related U.S. Application Data

[63] Continuation of Ser. No. 587,874, Jun. 18, 1975.

[30] Foreign Application Priority Data

Jun. 21, 1974 [GB] United Kingdom ............... 27636/74
Jun. 21, 1974 [GB] United Kingdom ............... 27637/74

[51] Int. Cl.² .............................................. B32B 3/30
[52] U.S. Cl. .................................. 428/167; 264/210 R; 264/DIG. 47; 428/134; 428/343

[58] Field of Search ............... 428/167, 169, 343, 140, 428/131, 134, 136; 24/16 PB; 264/147, 284, DIG. 47, 210 R; 156/167, 229, 209; 206/411; 427/207

[56] References Cited

U.S. PATENT DOCUMENTS

3,875,648   4/1975   Bone ..................................... 24/150

*Primary Examiner*—Stanley S. Silverman
*Attorney, Agent, or Firm*—Robert L. Goldberg; David G. Conlin

[57] ABSTRACT

A melt-embossed polymer film with primary parallel grooves on one surface and secondary parallel grooves on the other surface such that the combined tapes of the grooves is at least substantially equal to the film thickness, the two sets of grooves being located at an angle to each other of not less than 30°, is stretched at right angles to the direction of the primary grooves by a small amount to give a perforate product which can be formed into strips tearable longitudinally or transversely and thus useful as a vapor-permeable substrate for adhesive-coated tape.

9 Claims, 2 Drawing Figures

EMBOSSED FILM PRODUCT AND ADHESIVE COATED STRIP FORMED THEREFROM

This is a division of application Ser. No. 587,874 filed June 18, 1975.

This invention relates to adhesive tapes based on embossed film material.

British Pat. No. 1,110,051 described the production of net from a polymer film whereof one surface is provided with a set of parallel grooves or channels and the other surface is also provided with a set of parallel grooves or channels the direction of which intersects the direction of the first set. In such a film the channels are of such depth that the combined depth of the channels (on the two surfaces of the film) is a small amount less than the thickness of the film so that a thin continuous membrane is left at the points of intersection.

When such a film is stretched biaxially it splits at the thin intersection areas to provide an openwork net structure.

We have now discovered that if a certain type of such film is stretched exclusively or predominantly in one direction it has unexpected properties, and in particular provides a material which can be readily torn in either of two directions at right angles.

The present invention further envisages that such a material is particularly useful as a substrate for a strapping tape as used in a medical context.

In one aspect therefore the invention consists in a melt-embossed polymer film having on one surface a plurality of primary parallel ribs and grooves extending in a first direction and on the other surface a plurality of secondary parallel ribs and grooves extending in a second direction intersecting with the first direction at an angle of not less than 30° the combined depths of the grooves being equal to the film thickness, or only a small amount less than the film thickness so that a thin membrane is left at the areas of intersection, the secondary ribs and grooves being more closely spaced than the primary ribs and grooves and the film having been subjected to exclusively or predominantly uniaxial stress in a direction at right angles to the direction of the primary ribs and grooves.

Preferably the polymer film is produced by melt-embossing and the "first" direction may in such a case be the longitudinal or "machine" direction. It is however possible in such an instance for the primary grooves to be transverse and the secondary grooves to be longitudinal.

Suitable polymer materials include polymers of olefins, particularly of ethylene, and copolymers of olefins. High density polyethylene is particularly suitable.

The product described above is in the form of a film the substrate of which may be visibly perforate or may possess small incipient cracks across the expanded grooves. It is a totally unexpected property of this material that it can be cleanly torn transversely as well as longitudinally. That is to say, the tears propagate either in the first direction or in the direction of applied stress.

The reason for this is not fully understood. Similar tear propagation does not occur if the melt-embossed film is programmed by possessing a number of raised embossments on one or both surfaces, or programmed by possessing a number of discrete depressions or cavities in one or both surfaces, and then subjected to a similar uniaxial stress.

This property of readily tearing in either of two directions at right angles is exhibited over a wide range of film characteristics and groove sizes. Thus, the grooves on each surface may either terminate at their bases in a sharp line or in a flat base portion. It is preferable if the two sets of grooves are located at right angles.

Thus, in numerical terms a preferred product is a melt-embossed film or net product of the nature discussed above possessing on one side a pattern of primary grooves at a spacing of between 40 and 120 grooves per inch, and on the other side a pattern of secondary grooves at right angles at a spacing from 100 to 250 grooves per inch, but in any case smaller than the primary grooves.

For many purposes transverse stretch from 100 to 400% is adequate, and normally from 150 to 250% is preferred.

It is possible to produce such films without any stretch in the said first direction, which for melt-embossed film is usually the longitudinal or machine direction. However, it is preferred to stretch in the first direction to some extent especially when the ribs and grooves are relatively small size. Generally speaking the film can be given such a stretch of up to 100%. Thus it will be apparent that in the product of this invention it is preferred for one side to possess relatively large grooves in the machine direction and the other to possess relatively small grooves in the 90° transverse direction and for the film to be stretched more than 100% in the transverse direction and (if at all) less than 100% in the machine direction.

British Pat. No. 1,110,051 describes various methods by which suitable sheet can be produced. It is however preferred according to the invention to pass a molten film of polymer to the nip between two rollers. To produce a film of the characteristics described above one roller will preferably possess circumferential or helical ribs and grooves and the other roller will preferably possess axial ribs and grooves or possibly ribs and grooves angled at an angle up to 60° to the axial direction.

It will be apparent moreover that the invention extends not only to the film but also to a method of producing such films in which (a) a molten polymer is extruded as a film into the nip between two such rollers where it is simultaneously chilled and embossed with the requisite pattern, (b) the embossed film is stretched in the transverse direction (optionally with a small amount of machine-direction stretch) and (c) the film is cut or torn into strips in a longitudinal or transverse direction. Steps (b) (c) and (d) can be carried out in any order.

In a further aspect the invention consists in the material described above coated on at least one surface thereof with an adhesive, preferably a physiologically acceptable gaspermeable and watervapour-permeable adhesive.

Usually this is made available in the form of a tape.

The tape is preferably one having adhesive on one side only. A tape having adhesive on both sides may be used for attaching medical appliances to the skin or for joining two or more porous sheets to form a laminate that is also porous. Such a laminate may be used for example in clothing.

Adhesives for the tapes of the present invention are preferably pressure-sensitive adhesives. However, adhesives of other kinds may be used, for example, solvent-responsive or heat-sealing adhesives.

An acrylic resin may be used as the pressure-sensitive adhesive, particularly when the tape is to be used for medical purposes. Acrylic resins have reduced skin sensitation properties compared with, for example, rubber adhesives; also aqueous acrylic adhesives have a high MVP when spread as a continuous film.

If a rubber-based pressure-sensitive adhesive is to be used then the backing should first have a tie-coat or primer coat applied to it. Acrylic/rubber emulsions are examples of suitable tie-coats. If high-density polyethylene, the preferred material, is to be used is should usually have a surface treatment, for example by corona discharge, on the surfaces that are to be coated with adhesive.

The adhesive may be applied to the backing using conventional methods. For example, to produce a double-sided tape the backing may be run through a solution or emulsion of the adhesive and then dried. Alternatively the adhesive may be applied to one side of the backing, which is then protected with a removable liner while adhesive is applied to the other side.

Tape with adhesive on one side may be obtained simply by coating only the required side with adhesive for example, with a roller. Also, other known coating methods such as transfer coating, "tramline" coating, pattern coating, may be used.

After their manufacture, tapes according to the present invention may be cut to the required size then wound onto cores ready for use. To permit winding onto cores the tapes with adhesive on both sides require a removable liner on one side. Tapes with adhesive on one side may have the other side coated with a release coating.

The invention will be further described with reference to the accompanying drawings in which.

Figure 1:
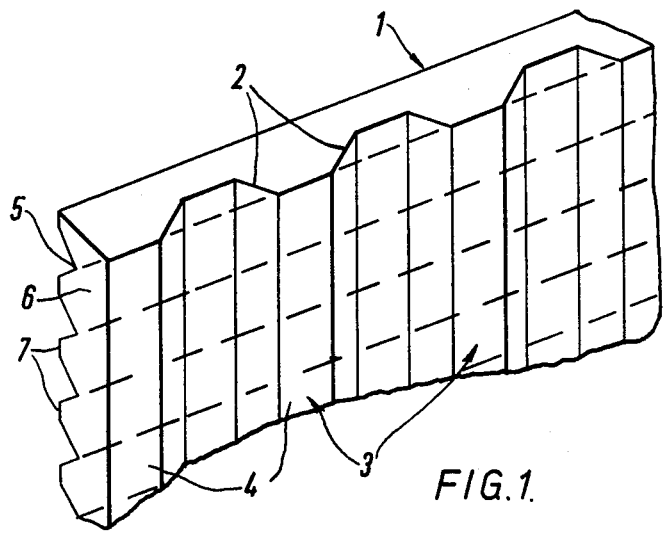
FIG. 1 shows a typical sheet of embossed film prior to stretching.

In FIG. 1 a sheet of polymer 1 is provided by melt-embossing with flat-bottomed grooves 2 defining between themselves longitudinal primary ribs 3. As shown, the flat-topped roller ribs used for melt embossing grooves 2 have not pressed deeply into the molten material and so leave a more or less flat top 4 to the ribs 3.

On the other surface of the film secondary grooves 5 separate and define secondary ribs 6 each with flat top 7.

The sheet of the configuration shown can be produced by passing a flat molten extruded film of polymer into the nip between a circumferentially grooved roller (to provide longitudinal primary ribs 3 and grooves 2) and an axially grooved roller (to provide transverse secondary ribs 6 and grooves 5), in which nip the film is simultaneously embossed, cooled, and solidified.

Figure 2:
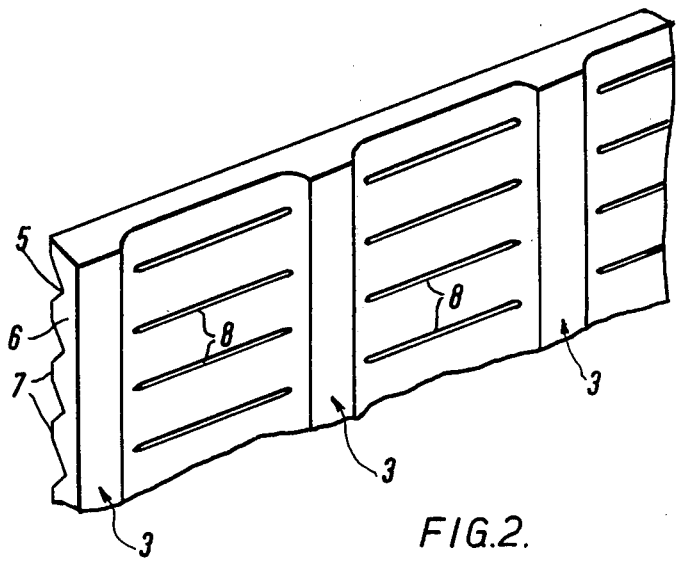
FIG. 2 shows a sheet after stretching.

FIG. 2 shows the effect of transverse stretch on a sheet of polymer as shown in FIG. 1. The thinner portions of the film, that is to say the grooves 2, are widened and deformed and give at least incipient cracking locations corresponding to the intersection areas of grooves 2 and grooves 5. These areas are shown at 8.

When this film is torn longitudinally it appears that the tear will propagate alongside a rib 3, where the respective "shoulder" areas (at the ends of the incipiently cracked portion) are contiguous weak areas and as such can allow the tear to run from one end to the other. When the film is torn transversely the tear appears to run through the cracked portions and through the ribs 3 separating them, joining up with the aligned cracked portion on the other side of the rib. This description and the mechanism of tearing is largely hypothetical and the Applicants, while believing it to be true, do not intend to limit their invention by this explanation.

The invention will be further described with reference to the following examples wherein Examples 1 and 2 describe production of the stretched film.

EXAMPLE 1

A high density polyethylene of melt flow index 6 was extruded as a molten film and embossed between two cooperating grooved rollers cooled to approximately 60°–70° C. One roller was provided with 100 circumferential grooves, triangular in cross-section, per transverse inch; the other with 250 grooves, triangular in cross-section, per circumferential inch, the solidified and embossed film being taken off over this latter roller.

The solidified grooved sheet tore easily in the machine direction but only with difficulty in the transverse direction. However, after stretching in the transverse direction by 116% it was possible to tear the resultant net in the transverse direction; 200% transverse stretch gave even better transverse tear characteristics.

EXAMPLE 2

A high density polyethylene of M.F.I. 6 was blended with 16.6% by weight of high impact polystyrene, extruded as a molten film and embossed between two cooperating grooved rollers cooled to approximately 60°–70° C. One roller was provided with 100 circumferential grooves per transverse inch, defined between flat topped roller ridges with, in cross-section 45° inwardly tapering sides and a flat top 0.004 inches in width, and the other roller with 250 grooves, triangular in cross-section with 80° included angle, per circumferential inch, lying at 35° to the longitudinal direction, the solidified and embossed film being taken off over this latter roller.

The resultant grooved sheet, of 100 longitudinal grooves per inch (measured in the transverse direction) tore easily lengthwise but only with difficulty transversely.

After forming a net by 200% transverse stretch (i.e. 3:1 stretch), splits occur at the transverse grooves to form bands which fibrillate to fibrous bands due to angled peel stress and the use of a polymer blend. The fibrous bands are oriented into the direction of the transverse stress.

Examination of the properties of this net gave the following results.

| Test methods | |
|---|---|
| Yield | SM.365. |
| Thickness | Mercer thickness gauge at 2 psi load. |
| Tensile strength | GM.12, 13"/min, 7 × 1" gauge length. |
| Tear strength | Special method based on rotating drum to simulate finger tear test. Results represent average load to tear through 5 cm of tape. |

-continued

| Porosity | Hydrostatic water test as described in Investigation Report IV/13A/5 dated August 1969. |
|---|---|

Physical properties of R.839T net. (as in Example 2)

|  |  | Left | Centre | Right |
|---|---|---|---|---|
| Yield (g/sq.m) |  | 39.2±6.1 | 38.9±7.3 | 34.8±4.4 |
| Strands/cm. | M.D. | 66.0±5.0 | 64.2±2.6 | 64.7±2.6 |
|  | T.D. | 19.2±0.6 | 20.2±0.6 | 18.3±0.6 |
| Thickness (thou) |  | 5.64±0.25 | 6.02±0.34 | 5.82±0.30 |
| Porosity: hydrostatic water pressure (cm) av. |  | 6 | 9 | 10 |
| Tear strength (g/sq.cm) av. | M.D. | 27.6 | 27.0 | 28.0 |
|  | T.D. | 27.5 | 27.5 | 24.0 |
| Breaking load (kg) | M.D. | 0.99±0.09 |  |  |
|  | T.D. | 1.14±0.04 |  |  |
| Extension at break (%) | M.D. | 9.4±0.7 |  |  |
|  | T.D. | 24.4±5.3 |  |  |

Similar films could be made from high density polyethylene containing 5% by weight of a titanium dioxide/low density polyethylene mixture, or from a polyurethane of polyamide starting material.

EXAMPLE 3

EVALUATION OF SURGICAL STRAPPING TAPES BASED ON NET OF EXAMPLES 1 and 2.

The two types of net described were converted into adhesive tapes by direct coating with an emulsion based adhesive. The adhesive used was N.580 (Rohm and Haas), thickened with Collacryl VL. This adhesive was chosen to give adequate adhesion to the net together with an acceptable unspooling tension. Both nets were "Corona" discharge treated before spreading to give improved keying of the adhesive to the nets. Subjectively the adhesive shows improved keying to the styrene based net. This observation is confirmed by the results of the wash trial where less adhesive is left on the skin than from the tape based on the all-polyethylene net.

| TEST RESULTS |  |  |
|---|---|---|
| Test | EX. 1 | EX. 2 |
| Base wt. (gsm) | 38–41 | 38–40 |
| Adh. wt. (gsm) | 35–36 | 28–32 |
| Tape wt. (gsm) | 73–77 | 66–72 |
| Gauge (inch) | 0.0066±0.0002 | 0.0062±0.0002 |
| Tensile strength (kg/cm) | 1.11±0.08 | 0.91±0.11 |
| Elongation at break (%) | 11.6±3.5 | 7.5±2.1 |
| Elmendorf tear (g/strip) | 33±2 | 33±1 |
| Adh. to steel (g/cm) | 220±21 | 201±22 |
| Adh. to self (g/cm) | 39±5 | 24±9 |
| Hold test (1 kg) | 8 hrs | 8 hrs |
| Unspooling tension (g/cm. at 50 ft/min.) | 70–89 | 89–147 |
| MVP (g/sq.m./24 hr/40° C at 100-20% r.h.) | 318±17 | 419±16 |
| Holes per 10 sq. cm. | 0–2 | 0–1 |
| Wear trial efficiency (%) | 59 | 73 |
| Adhesive residue (%) | 0 | 0 |
| Wash trial efficiency (%) | 60 | 87 |
| Adhesive residue (%) | 70 | 26 |

We claim:

1. A polymer film having low tear resistance both in a longitudinal direction and in a transverse direction, said film having been produced by melt embossing and having on one surface a plurality of primary parallel ribs and grooves extending in a longitudinal direction at a spacing of from about 40 to 120 grooves per inch, and on the other surface a plurality of secondary parallel ribs and grooves extending in a secondary direction intersecting with the longitudinal direction at an angle of at least 30° and at a spacing which is from about 100 to 250 grooves per inch; the combined depths of the grooves being substantially equal to the film thickness; the secondary ribs and grooves being more closely spaced than the primary ribs and grooves; and the film having been subjected to at least predominantly uniaxial stress in a direction at right angles to the longitudinal direction by stretching from about 100% to 400%.

2. A polymer film as claimed in claim 1 in which the two sets of grooves are located at right angles.

3. A film as claimed in claim 1 in which the degree of stretch is from 150 to 250%.

4. A film as claimed in claim 1 in which stress is also imparted in a longitudinal direction by stretching not more than 100%.

5. A polymer film as claimed in claim 1 composed of an olefinic polymeric material.

6. A polymer film as claimed in claim 5 in which the polymer is high density polyethylene.

7. A polymer film as claimed in claim 1 in the form of a tape coated on only one surface thereof with a physiologically acceptable, gas-permeable and water vapor-permeable pressure-sensitive adhesive.

8. A polymer film as claimed in claim 7 in which the pressure-sensitive adhesive is an acrylic resin.

9. A polymer film as claimed in claim 7 in which the pressure-sensitive adhesive is a rubber-based pressure-sensitive adhesive applied over a tie-coat of an acrylic resin/rubber emulsion.

* * * * *